United States Patent [19]
Foshee et al.

[11] Patent Number: 5,732,806
[45] Date of Patent: Mar. 31, 1998

[54] COMPENSATOR TO PREVENT BACKLASH IN A SURGICAL INSTRUMENT

[75] Inventors: David L. Foshee, Apex; Stephen J. Dawes, Raleigh, both of N.C.; Jan Steuperaert, Le Faget, France

[73] Assignee: Pilling Weck, Incorporated, Research Triangle Park, N.C.

[21] Appl. No.: 624,171

[22] Filed: Mar. 29, 1996

[51] Int. Cl.⁶ ............................ F16D 11/00; A61B 17/068
[52] U.S. Cl. ........................ 192/30 R; 74/575; 227/175.1
[58] Field of Search ............................ 227/175.2, 175.1, 227/182.1; 606/143; 192/30 R; 74/575

[56] References Cited

U.S. PATENT DOCUMENTS 5,344,061  9/1994  Crainich ............................ 227/182.1
5,413,272  5/1995  Green et al. ........................ 227/175.1
5,484,095  1/1996  Green et al. .................... 227/175.1 X
5,560,532  10/1996  DeFonzo et al. ............... 227/175.1 X

*Primary Examiner*—Rodney H. Bonck
*Attorney, Agent, or Firm*—Rosenblatt & Redano P.C.

[57] ABSTRACT

The present invention provides a surgical instrument which prevents backlash due to reduction of applied force on the handle or trigger of the surgical instrument. The instrument includes a clutch system that is adapted to maintain the position of the portion of the driver that is in mechanical communication with the forming tool upon reduction of the applied force.

10 Claims, 4 Drawing Sheets

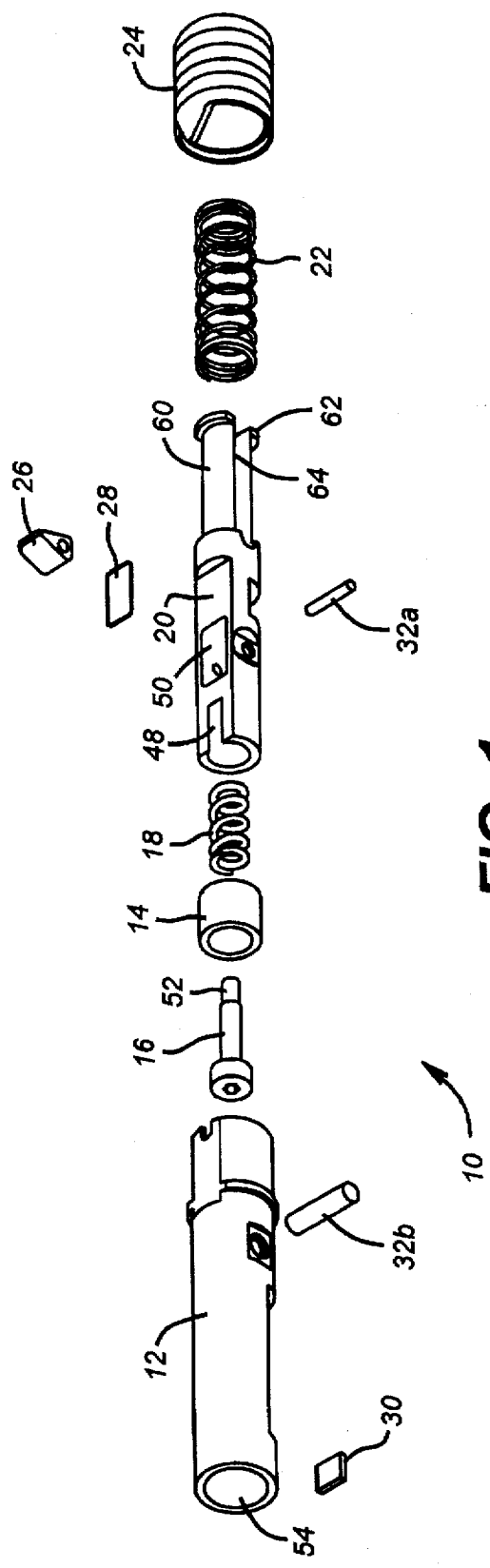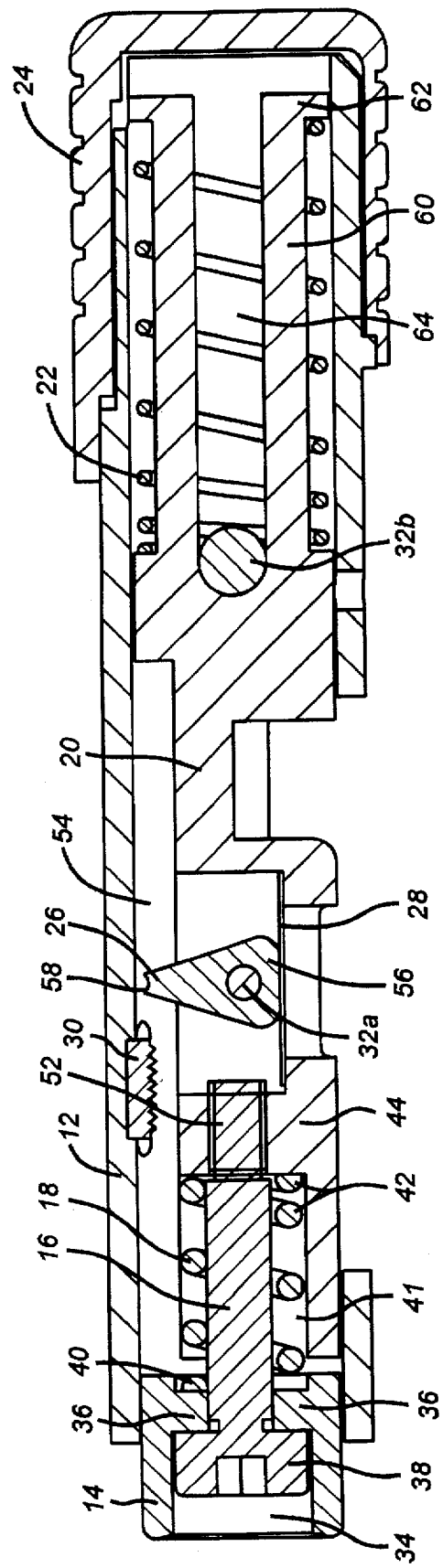

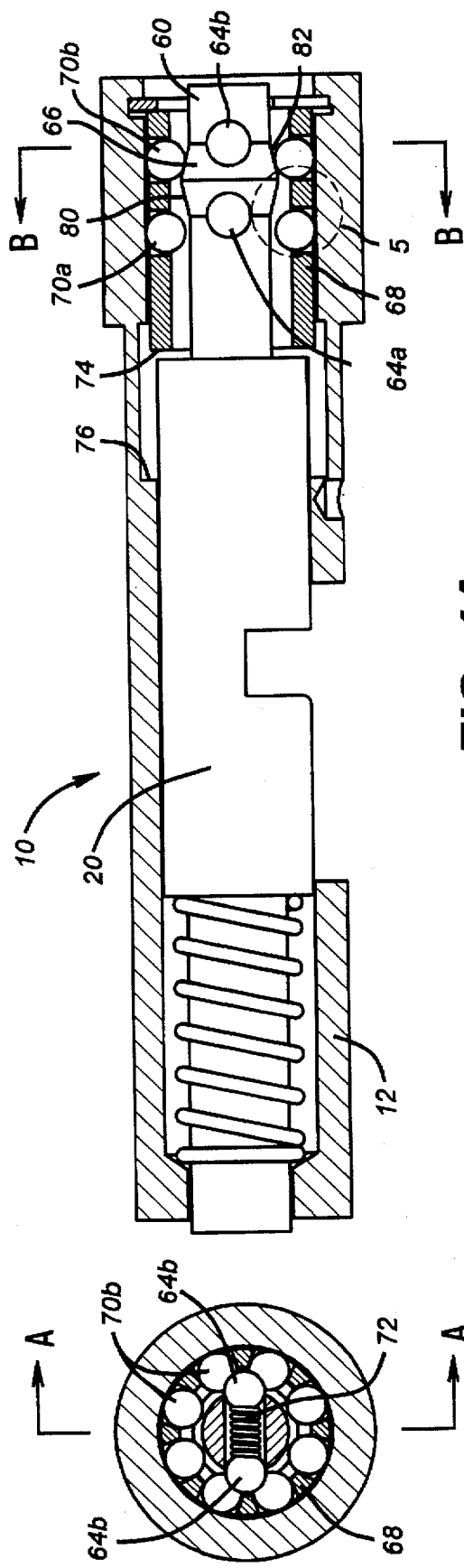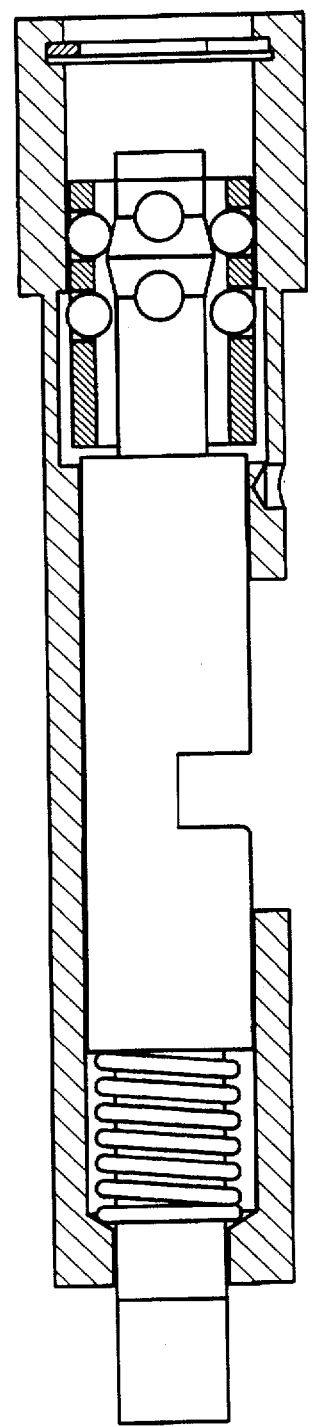
FIG. 4A
FIG. 4B
FIG. 4C

COMPENSATOR TO PREVENT BACKLASH IN A SURGICAL INSTRUMENT

FIELD OF THE INVENTION

The present invention relates to surgical instruments, particularly to instruments used in surgery to apply surgical staples.

BACKGROUND OF THE INVENTION

Surgery frequently requires the application of surgical staples or other instruments which can ligate, grab or rip tissue or other materials. Such instruments must be simple in construction, reliable in operation, and low in cost. Instruments that contact internal organs also must be capable of sterilization. Alternately, the instruments must be sufficiently low in cost that they may be disposed of after a single use.

Surgical instruments should give the surgeon good feedback during a procedure to allow as much control as possible during use of the instruments. If component systems are used, the components should be securely attached to one another to avoid disconnection during the procedure.

One of the problems encountered using a surgical stapler is that a staple must be dispensed from the staple cartridge and then retained securely within the jaws of the instrument until after the staple has been closed around a desired target. A delicate balance must be struck to securely retain the staple between the jaws while still permitting sufficient freedom of movement to position the staple around the desired target. This balance is even more difficult to attain because surgeons often tend to release or loosen their grip on the handles or other actuating means while positioning the staple around the target. To counteract this tendency, the instrument must be equipped to retain the staple in the jaws in spite of the release of pressure on the handle.

Typically, the staple is retained in the jaws by a clutch system. One such clutch system consists of a rack mounted on a stationary surface in the handle or actuating means. The teeth of the rack engage a pawl that is rockably mounted on a driver. Typically, a constant proximal force is exerted on the driver and pawl via a return spring. When the user squeezes the handle or trigger, the driver is driven distally relative to the rack. When the pawl reaches the rack, the tip of the pawl engages the teeth on the rack.

If the distal movement of the driver stops before the pawl clears the rack—for example, if the surgeon's grip on the handle loosens, then the return spring forces the tip of the pawl back against the teeth of the rack and holds the driver in position. The engagement between the teeth and the pawl prevents the driver from being pulled proximally by the return spring. When the trigger is later squeezed, the pawl and the driver move distally until the pawl clears the rack. At this time, the only force on the driver and pawl will be the return spring, and the pawl is pulled proximally over the teeth until it clears the rack and begins another cycle.

Unfortunately, even using such a clutch system, some relative movement between the teeth and the pawl is required in order to prevent the clutch system from jamming. This slight relative movement—sometimes called backlash—creates a danger that the staple will be released before it is closed over a desired target.

SUMMARY OF THE INVENTION

The present invention provides a system to prevent backlash due to reduction of applied force on the handle or trigger of a surgical instrument. The system includes a clutch that is adapted to maintain the position of the portion of the driver that is in mechanical communication with the forming tool upon reduction of said applied force.

BRIEF DESCRIPTION OF THE DRAWINGS

FIG. 1 is an exploded view of a surgical stapler incorporating the present invention.

FIG. 2 is a longitudinal cross section of the surgical stapler of FIG. 1.

FIGS. 4A and 4C are longitudinal cross sections of a surgical stapler using an alternate embodiment of the present invention.

FIG. 4B is an axial cross section along line B—B of FIG. 4A.

DETAILED DESCRIPTION OF THE INVENTION

Figure 3A:
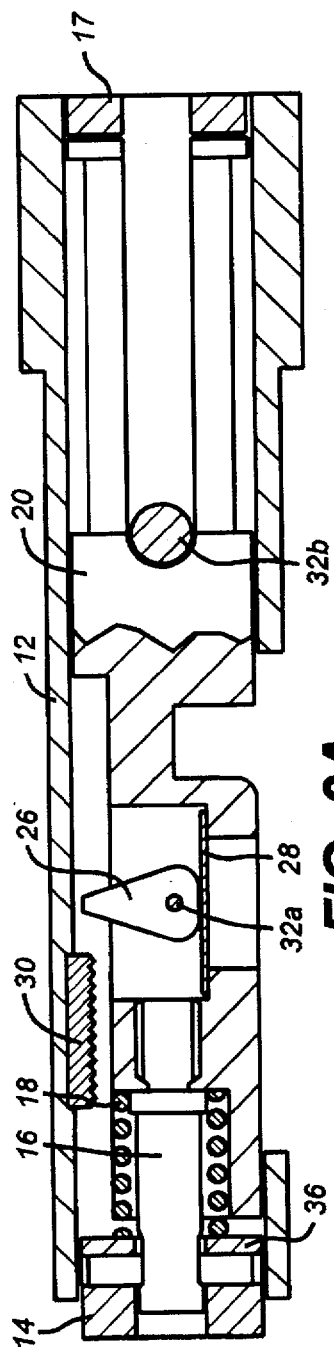
FIGS. 3A—3C are longitudinal cross sections of the surgical stapler of FIGS. 1 and 2 in various stages of operation.

The invention will be described with reference to the accompanying drawings. FIG. 1 is an exploded view of relevant portions of a stapler 10 with a pawl and ratchet clutch system which also incorporates the present invention. Although the present invention is described with reference to a surgical stapler, the principles of the present invention may be applied to substantially any surgical instrument to prevent backlash of movable members. Furthermore, with respect to surgical staplers, the invention may be used in substantially any clip applier that uses a member movable relative to an applier body to close a clip.

The major portions of the stapler that are relevant to the present invention are an outer sleeve 12, a driver nose 14, a nose screw 16, a nose spring 18, a driver 20, a driver spring 22, an end cap 24, a pawl 26 and its associated pawl spring 28, and a rack 30. These components are held together, when assembled, by two assembly pins 32a and 32b. The foregoing components are made of stainless steel. With the exception of the nose spring 18 and the driver spring 22, a preferred stainless steel is 17-4 PH stainless steel. A preferred stainless steel for the nose spring is 17-7 PH stainless steel, which is stronger than 17-4 stainless steel. A preferred stainless steel for the driver spring is 300 series stainless steel.

The components are shown in cross section after assembly in FIG. 2. Beginning at the distal end, the distalmost portion of the assembly is the driver nose 14. The driver nose 14 has a bore 34 therethrough, and an axial shoulder 36 formed at its proximal end. The distal surface of the shoulder 36 abuts the proximal edge of a corresponding opposed shoulder 38 formed at the proximal end of the nose screw 16. The nose spring 18 concentrically surrounds the nose screw 16 and is held within the bore 41 at the distal end of the driver 20. The proximal portion 42 of the nose spring 18 abuts an axial shoulder 44 in concentric bore 41 through the distal end of the driver 20. The proximal end 52 of the nose screw 18 has a reduced diameter and is retained in a bore through the shoulder 44, preferably by threading.

The amount of pressure that is exerted on the shoulder 36 by the nose spring 18 is a function of the load on the form tool and on the cartridge at "precock" position. In "precock"

position, the pawl 26 is engaged with the teeth of the rack 30. The amount of pressure exerted by the nose spring 18 on the shoulder 36 should be more than the load applied on the staple by the formtool spring, but less than the cartridge load (or the load on the formtool spring plus the staple forming load) at precock position.

In the illustrated embodiment, and as seen more clearly in FIG. 1, a portion of the outer surface of the distal end of the driver 20 has been cut away to form a flattened surface 46. This flattened surface 46 has two openings, a distal opening 48 and a median opening 50. The proximal end 60 of the driver 20 has a reduced diameter, is bisected by a longitudinal slot 64, and ends in an axial shoulder 62. The driver spring 22 concentrically surrounds the proximal end of the driver 20, and abuts the axial shoulder 62. The proximal end of the driver spring 22 and driver 20 are housed within an end cap 24. The outer sleeve 12 is secured around the driver 20 by the assembly pin 32b, which is held within the longitudinal slot 64.

The pawl 26 is held within the median opening 50 in the driver 20 by the assembly pin 32a. The pawl 26 has a blunt end 56 which abuts a pawl spring 28 and, preferably, a serrated upper end 58 for engaging the teeth on the rack 30. The pawl spring 28 exerts force against the blunt end 56 of the pawl 26 to hold the upper end 58 of the pawl 26 against the rack teeth when the instrument is in the precock position.

Referring to FIG. 2, the rack 30 is affixed to the inner surface 66 of the bore 54 through the outer sleeve 12, preferably using a biocompatible glue, such as Trabanol FDA 22 epoxy. The driver 20 is positioned within the bore 54 so that the upper end 58 of the pawl 26 will abut the teeth on the rack 30 upon actuation.

The foregoing assembly may be used in conjunction with any suitable actuating means and forming tool as long as (a) the actuating means is capable of exerting sufficient force on the proximal end of the driver 20 to actuate the forming tool, and (b) the forming tool is capable of closing a staple around a desired target.

Figure 3B:
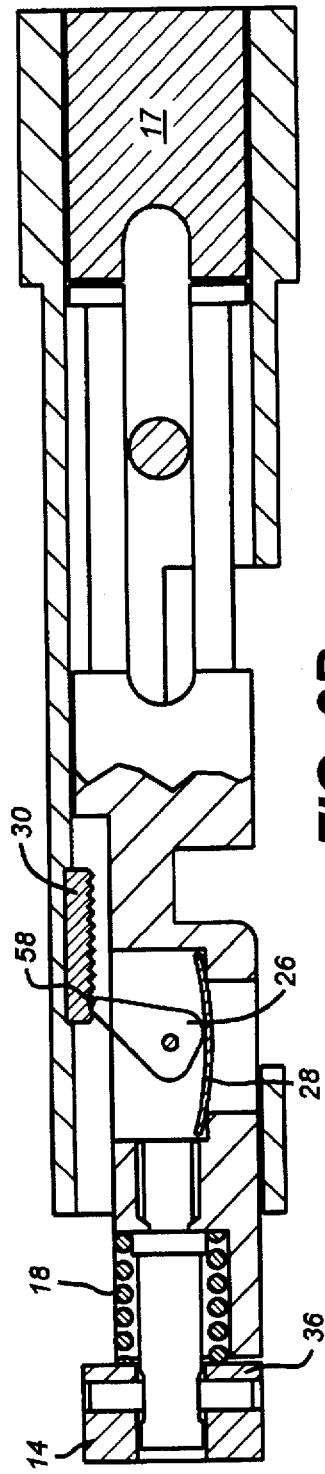
Figure 3C:
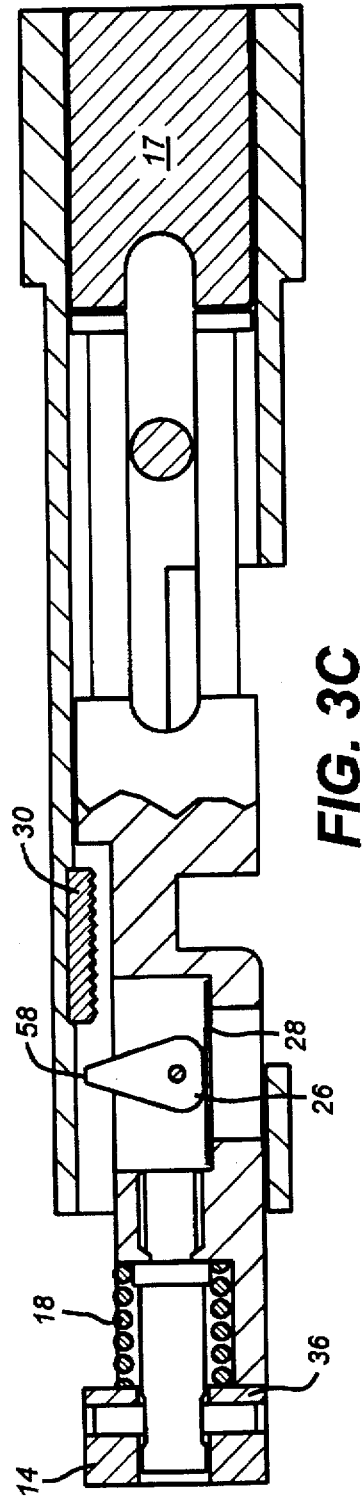

The operation of the described embodiment will be better understood with reference to FIGS. 3A–3C. Before actuation (FIG. 3A), the pawl 26 is located proximal to the rack 30, and the nose spring 18 is in its most extended state. Upon actuation, e.g., by squeezing a handle, which is part of actuating mechanism 17 shown schematically in FIGS. 3A–3C the upper end 58 of the pawl 26 engages and moves distally across the teeth on the rack 30. The pawl spring 28 biases the pawl 26 toward the rack 30 to ensure such engagement.

If the user releases the handle, or loosens the tension on the handle, the driver 20 will be pulled proximally by the driver spring 22 (not shown), and the upper end 58 of the pawl will move proximally until it is jammed against the adjacent tooth on the rack 30. This proximal motion will be compensated for by the nose spring 18, which will exert a constant force on the shoulder 36 of the driver nose 14. The force on the shoulder 36 will be sufficient to retain the driver nose 14 in substantially the same distal position, thereby preventing proximal movement and accidental release of a staple by the formtool.

An alternate embodiment of a stapler incorporating the present invention is shown in FIGS. 4A–4C, in which like structures will be referred to by like numerals. The stapler 10 includes an outer sleeve 12, a driver 20, and a driver spring 22 (not shown). At its proximal end 60, the driver 20 has a reduced diameter portion with a tapered shoulder 66. At proximal and distal ends of the tapered shoulder 66 are diametrically opposed steel balls 64a, 64b. A proximal sleeve 68 is provided around the proximal end 60 of the driver 20. As seen more clearly in FIG. 4B, the steel balls form integral concentric rings 70a, 70b around the proximal sleeve 68. The diametrically opposed steel balls 64a and 64b are biased apart by a spring 72. At its widest point, the tapered shoulder 66 on the driver 20 has a diameter wider than the distance between the inner surface of the diametrically opposed concentric steel balls in rings 70a and 70b. Similarly, the diametrically opposed steel balls 64a and 64b are biased apart by the spring 72 to a distance between their outer surface that is wider than the distance between the inner surface of the diametrically opposed concentric steel balls in the rings 70a and 70b. As a result, the proximal end 60 of the driver 20 is supplied with the following camming surfaces: the outer surface of the distal diametrically opposed steel balls 64a; the surfaces 80, 82 of the tapered shoulder 66; and, the outer surface of the proximal diametrically opposed balls 64b.

Figure 5:
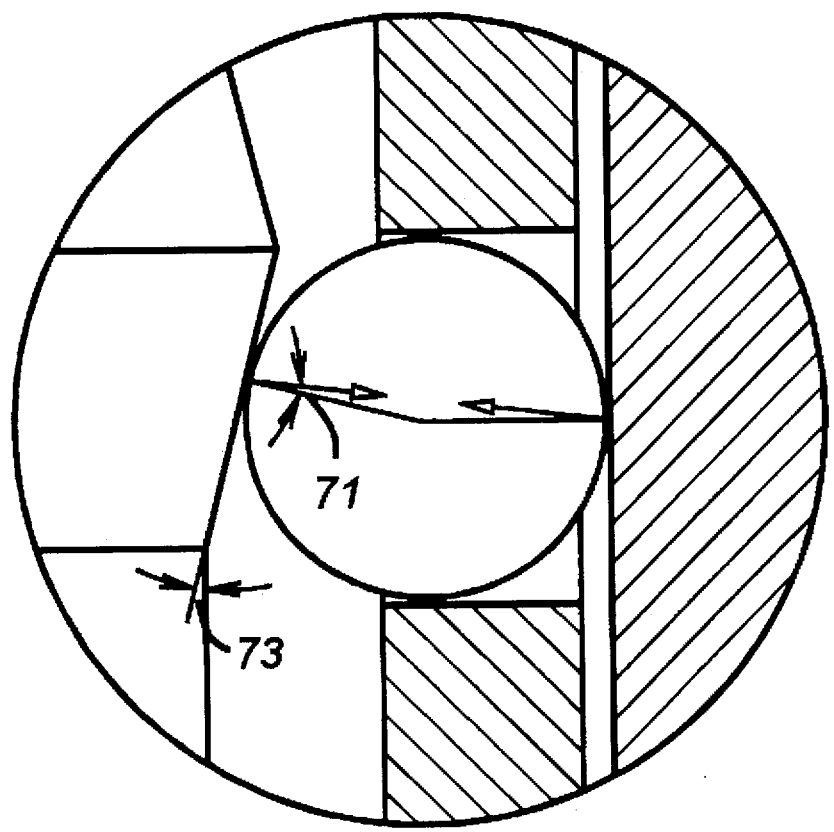
FIG. 5 is a detail of the ring of spheres encountering the taper, illustrating in more detail the contact angle between the sphere and taper as compared to the taper angle, all of which is shown in more detail in FIGS. 4A-4C.

At rest, the balls in the concentric rings 70a, 70b are pushed against the surfaces 80, 82 of the shoulder 66 and the inner surface of the outer sleeve 12. The force applied by the outer surface of the diametrically opposed steel balls 64a, 64b against the inner surface of the balls in concentric rings 70a, 70b—which is also the force that holds the balls in rings 70a, 70b against the surfaces 80, 82 of the shoulder 66 and sleeve 12—is relatively small. The surfaces 80, 82 of the shoulder 66 and the inner surface of the outer sleeve 12—apply the two main forces to the balls in rings 70a, 70b—and can be considered to "face" one another. Geometrically, the forces applied by these surfaces (80,82 v. 12) have an angle 71 (FIG. 5) from the normal that is half the angle 73 (FIG. 5) of the shoulder 66 from the normal. In a preferred embodiment, the angle 71 is about 7°. Maintaining the angle 71 smaller than the friction angle prevents the balls in rings 70a, 70b from sliding. The friction angle= arctan (coefficient of friction), which for stainless steel is approximately 8°.

If force is applied to the driver 20 in the distal direction, the compressive force on the balls in rings 70a, 70b increases, but the lateral force on the balls in rings 70a, 70b does not increase. As a result, the system is blocked. The small force applied by the balls 64a, 64b pushes the rings 70a, 70b slightly distally, making the blockage worse. When the shoulder 66 moves distally, the balls 64a, 64b pull the rings 70a, 70b distally. When the distal shoulder 74 of the sleeve 68 hits the shoulder 76, the balls 64a, 64b are pushed inward by the balls in rings 70a, 70b, allowing balls 64a, 64b to pass distally over the balls in rings 70a, 70b. Because of the angle 71, which is preferably about 7°, the forces on the balls in rings 70a, 70b are high, and can mark the surface of the shoulder 66 or sleeve 12 if not divided by "8." Misalignment of the balls in rings 70a, 70b also can introduce other forces that disturb the system and make the balls in rings 70a, 70b slide on the surface(s). Therefore, the balls in rings 70a, 70b must be very well aligned with the shoulder 66 so that all of the balls in the rings 70a, 70b contact the shoulder 66.

In the resting position, the balls 64a lie between the two concentric rings of balls 70a and 70b. In operation, the actuating means pulls the driver 20 distally until the balls 64a, 64b are compressed and the sleeve 68 holding the concentric rings of steel balls 70a and 70b pops over and moves proximal to the balls 64a. The spring 72 keeps the balls 64b tensioned against the concentric rings of balls 70a, 70b, holding the concentric ring of balls 70a tightly in place against the distalmost tapered surface 80 of the shoulder 66.

Once the driver 20 completes its forward movement, and a staple is compressed around a desired target, the driver spring 22 forces the driver proximally. The spring 72 keeps the balls 64a tensioned against the concentric ring of balls 70a until the proximal force on the driver 20 overcomes the tension applied by the spring 72, permitting the sleeve 68 to pop over and move distally to the balls 64a. The spring 72 keeps the balls 64b tensioned against the concentric ring of balls 70b, holding the concentric ring of balls 70b tightly in place against the proximal tapered surface 82 of the shoulder 66. Because of the close engagement between the balls 64a, 64b, the concentric rings of balls 70a, 70b, and the tapered surfaces of the shoulder 66, substantially no backlash is experienced if the user releases or loosens the grip on the handle or other actuating means during this operation.

Persons of ordinary skill in the art will appreciate that many modifications may be made to the embodiments described herein without departing from the spirit of the present invention. Accordingly, the embodiments described herein are illustrative only and are not intended to limit the scope of the present invention.

We claim:

1. An apparatus for removal of backlash from a surgical instrument, comprising:

a body having a proximal and a distal end;

an actuating mechanism on said body;

an actuating assembly having a proximal component connected to said actuating mechanism and a distal component movably mounted with respect to said proximal component;

said actuating assembly operable from a distal to a proximal position against a return bias member acting thereon to return said actuating assembly from said distal to said proximal position;

a clutch mounted to said proximal component to selectively arrest proximal movement of said proximal component, beyond a predetermined proximal backlash movement, due to said bias member of said actuating mechanism;

a biasing component acting on said distal component to bias it distally with respect to said proximal component when said proximal component is arrested by said clutch to compensate for said backlash movement.

2. The apparatus of claim 1, wherein said biasing component comprises a spring.

3. The apparatus of claim 2, wherein said clutch comprises:

a pawl mounted to said proximal component;

a rack mounted to said body having teeth;

said pawl pivotally mounted to ratchet over said teeth when moved distally and to be captured by said teeth upon a proximal backlash movement if said actuating mechanism is released before said pawl is advanced proximally beyond said teeth.

4. The apparatus of claim 3, wherein said bias member comprises a spring acting on said actuating assembly.

5. The apparatus of claim 1, wherein:

cessation of distal advancement of said actuating mechanism before a predetermined value allows said biasing component to exert a distal bias force on said distal component with said clutch arresting proximal movement of said proximal component;

said distal bias force is sufficient to hold the position of said distal component without substantial further distal advancement until said actuating mechanism readvances said actuating assembly distally.

6. An apparatus for removing backlash in a surgical instrument, comprising:

a body having a proximal and a distal end;

an actuating assembly movably mounted in said body for reciprocation toward said proximal and distal end points to actuate the surgical instrument;

a clutch assembly further comprising:
      at least one taper on said actuation assembly;
      a movable sleeve around said actuating assembly, supporting at least one first projection;

said actuating assembly comprising at least one second projection;

whereupon said second protection engages said first projection to allow movement of said actuating assembly with said sleeve toward a distal end point and if distal movement stops short of said distal end point, said first projection engages said taper to prevent substantial proximal movement of said actuating assembly by wedging it against said body until distal movement of said actuating assembly resumes and said distal end point is reached.

7. The apparatus of claim 6, wherein:

said first projection comprises two spaced-apart rings of spheres retained by said sleeve and in rolling contact therewith;

said second projection comprises spaced-apart biased spheres that can selectively engage said rings of spheres and, when said bias is overcome, pass through said rings of spheres.

8. The apparatus of claim 7, wherein:

said actuating member comprises a proximal taper and a distal taper, with said biased spheres extending through each of said tapers;

said biased spheres on said distal taper driving a distally oriented ring of said spheres on said sleeve to obtain distal movement of said actuating assembly in tandem with said sleeve.

9. The apparatus of claim 8 wherein:

said body provides a distal travel stop for said sleeve whereupon contact of said sleeve with said travel stop, said distally oriented biased spheres, which had been in rolling contact with said distally oriented ring of spheres, move beyond said distally oriented ring of spheres on said sleeve and distal movement of said actuating member is concluded as said distal taper contacts said distally oriented ring of spheres on said sleeve.

10. The apparatus of claim 9, wherein:

said body provides a proximal travel stop for said sleeve whereupon proximal movement of said actuating member accomplished by said proximally oriented biased spheres rolling with said proximally oriented ring of spheres, said sleeve engages said proximal travel stop and said proximally oriented biased spheres pass through said proximally oriented ring of spheres to allow contact of said proximally oriented ring of spheres with said proximal taper which arrests the proximal movement of said actuating member against said body.

* * * * *